United States Patent
Nakanishi et al.

[11] 3,931,199
[45] Jan. 6, 1976

[54] BENZOPYRANO AND BENZOTHIOPYRANO [2,3-6] PYRIDINES

[75] Inventors: Michio Nakanishi; Takanori Oe, both of Nakatsu; Mineo Tsuruda, Shiida, all of Japan

[73] Assignee: Yoshitomi Pharmaceutical Industries, Ltd., Osaka, Japan

[22] Filed: Mar. 19, 1974

[21] Appl. No.: 452,574

[30] Foreign Application Priority Data
Mar. 19, 1973   Japan.............................. 48-32109
Nov. 8, 1973   Japan............................ 48-134214
Jan. 10, 1974   Japan.............................. 49-6376
Jan. 10, 1974   Japan.............................. 49-6377

[52] U.S. Cl................ 260/294.8 B; 260/287 CF; 260/294.9; 260/295 T; 260/295.5 R; 260/296 T; 260/297 T; 424/258; 424/263
[51] Int. Cl.².............. C07D 491/08; C07D 513/08
[58] Field of Search....... 260/295 T, 297 T, 294.8 B

[56] References Cited
UNITED STATES PATENTS
3,803,153   4/1974   Villani............................ 260/297 T OTHER PUBLICATIONS
Dean et al., "Chem. Abstracts" Vol. 52, (1958), pp. 4622–4623.

*Primary Examiner*—Henry R. Jiles
*Assistant Examiner*—Robert W. Ramsuer
*Attorney, Agent, or Firm*—Sughrue, Rothwell, Mion, Zinn & Macpeak

[57]   ABSTRACT
Heterocyclic compounds of the formula:

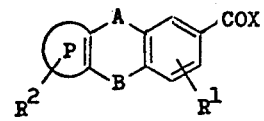

wherein A is a carbonyl group, a methylene group or an alkylidene group having 2 to 4 carbon atoms; B is an oxygen atom, a sulfur atom or —N(R')— (wherein R' is a hydrogen atom or an alkyl group having 1 to 4 carbon atoms); each of $R^1$ and $R^2$ is a hydrogen atom, a halogen atom, an alkyl group having 1 to 4 carbon atoms, an alkoxy group having 1 to 4 carbon atoms or a phenyl group which may be substituted by a halogen atom, an alkyl group having 1 to 4 carbon atoms or an alkoxy group having 1 to 4 carbon atoms; X is an alkyl group having 1 to 4 carbon atoms, a cycloalkyl group having 3 to 6 carbon atoms or OM (wherein M is a hydrogen atom, an alkyl group having 1 to 4 carbon atoms, a metal atom or $NH_4$); and ring P represents a pyridine ring, are useful as anti-allergic agents.

11 Claims, No Drawings

BENZOPYRANO AND BENZOTHIOPYRANO [2,3-b] PYRIDINES

This invention relates to novel and therapeutically valuable compounds of the formula:

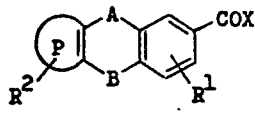  [I]

wherein A is a carbonyl group, a methylene group or an alkylidene group having 2 to 4 carbon atoms; B is an oxygen atom, a sulfur atom or —N(R')— (wherein R' is a hydrogen atom or an alkyl group having 1 to 4 carbon atoms); each of $R^1$ and $R^2$ is a hydrogen atom, a halogen atom, an alkyl group having 1 to 4 carbon atoms, an alkoxy group having 1 to 4 carbon atoms or a phenyl group which may be substituted by a halogen atom, an alkyl group having 1 to 4 carbon atoms or an alkoxy group having 1 to 4 carbon atoms; X is an alkyl group having 1 to 4 carbon atoms, a cycloalkyl group having 3 to 6 carbon atoms or OM (wherein M is a hydrogen atom, an alkyl group having 1 to 4 carbon atoms, a metal atom or $NH_4$); and ring P represents a pyridine ring.

In the above definition, the alkyl group includes methyl, ethyl, propyl, isopropyl and butyl; the alkoxy group includes methoxy, ethoxy, propoxy, isopropoxy and butoxy; the alkylidene group includes ethylidene, propylidene, isopropylidene and butylidene; the cycloalkyl group includes cyclopropyl, cyclobutyl, cyclopentyl and cyclohexyl; the halogen atom includes F, Cl and Br; and the metal atom among others includes Na, K and Al.

The ring system:

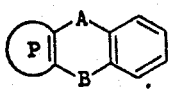

in the above formula [I] and also hereinafter represents any of the following structures (1)–(4).

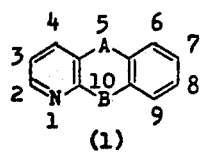
(1)

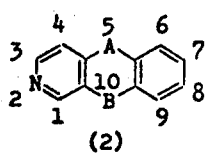
(2)

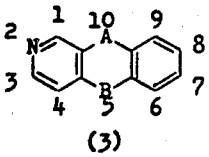
(3)

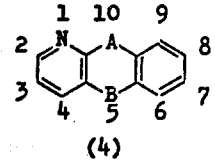
(4)

The compounds of formula [I] can be produced, for example, by the following methods:

I. In the case of compounds of formula [I] wherein X is an alkyl group or a cycloalkyl group;

a. By subjecting a compound of the formula:

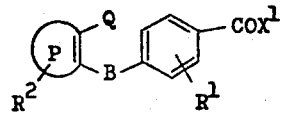  [II]

to intramolecular condensation, wherein B, $R^1$, $R^2$ and ring P are as defined above, $X^1$ is an alkyl group having 1 to 4 carbon atoms or a cycloalkyl group having 3 to 6 carbon atoms, and Q is a carboxyl group or a haloformyl group (e.g. —COCl or —COBr).

The condensation is usually carried out in an inert solvent (e.g. nitrobenzene, carbon disulfide or tetrachloroethane) at 20°–200°C, preferably in the presence of a condensing agent (e.g. aluminum chloride, ferric chloride, zinc chloride, polyphosphoric acid, sulfuric acid, phosphoryl trichloride, phosphorus trichloride or boron trifluoride).

According to the method (a), the compound of formula [I] wherein A is a carbonyl group can be obtained.

b. By actylating a compound of the formula:

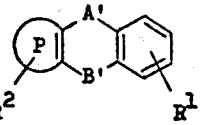  [III]

wherein $R^1$, $R^2$ and ring P are as defined above, A' is a methylene group or an alkylidene group having 2 to 4 carbon atoms, and B' is an oxygen atom, a sulfur atom or —N(R")— (wherein R" is an alkyl group having 1 to 4 carbon atoms), with an acid of the formula:

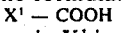
$X^1$ — COOH  [IV]

wherein $X^1$ is as defined above, or a functional derivative thereof (e.g. acid halide or acid anhydride).

The acylation is usually carried out with or without an inert solvent (e.g. nitrobenzene, carbon disulfide or tetrachloroethane) at 0°–150°C, preferably in the presence of Friedel-Crafts catalyst (e.g. aluminum chloride, ferric chloride, zinc chloride, polyphosphoric acid or sulfuric acid).

According to the method (b), the compound of formula [I] wherein A is a methylene group or an alkylidene group having 2 to 4 carbon atoms and B is an oxygen atom, a sulfur atom or —N(R")— (wherein R" is an alkyl group having 1 to 4 carbon atoms) can be obtained.

c. By hydrolyzing and decarboxylating a compound of the formula:

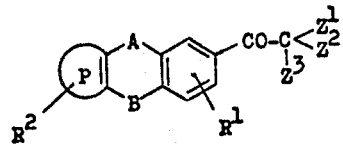  [V]

wherein A, B, $R^1$, $R^2$ and ring P are as defined above, $Z^1$ is $COOR^3$ ($R^3$ being an alkyl group), $CONH_2$ or CN, $Z^2$ is a hydrogen atom, an alkyl group, $COOR^3$, $CONH_2$ or CN, and $Z^3$ is a hydrogen atom or an alkyl group. In case that $Z^2$ is a hydrogen atom or an alkyl group, the aggregate number of the carbon atoms contained in $Z^2$ and $Z^3$ does not exceed 3.

The reaction is usually carried out with or without an inert solvent (e.g. water, acetic acid, dioxane or a mixture thereof) at 20°–150°C, preferably in the presence of an acid catalyst (e.g. hydrochloric acid, sulfuric acid or phosphoric acid).

According to the method (c), the compound of formula [I] wherein X is an alkyl group having 1 to 4 carbon atoms can be obtained.

d. By oxidizing any of compounds of the formulae:

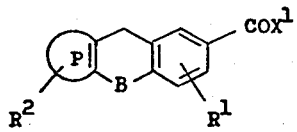   [Ia]

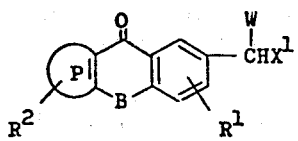   [VI]

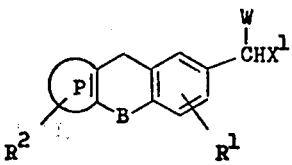   [VII]

wherein B, R¹, R², X¹ and ring P are as defined above, and W is a hydrogen atom, a hydroxyl group or a halogen atom (e.g. F, Cl or Br).

The oxidation is usually carried out in the presence of an oxidizing agent (e.g. permanganate, chromic acid, nitric acid, manganese dioxide, selenium dioxide or air), if necessary, in an inert solvent (e.g. acetone, pyridine, water, dioxane, benzene, chloroform, acetic acid or a mixture thereof).

According to the method (d), the compound of formula [I] wherein A is a carbonyl can be obtained.

II. In the case of compounds of formula [I] X is OM;

e. By subjecting a compound of the formula:

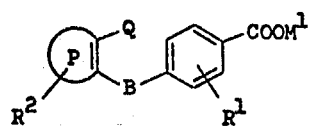   [VIII]

to intramolecular condensation, wherein B, R¹, R², Q and ring P are as defined above, and M¹ is a hydrogen atom or an alkyl group having 1 to 4 carbon atoms.

The condensation is usually carried out in an inert solvent (e.g. nitrobenzene, carbon disulfide or tetrachloroethane) at 20°–200°C, preferably in the presence of a condensing agent (e.g. aluminum chloride, ferric chloride, zinc chloride, polyphosphoric acid, sulfuric acid, phosphoryl trichloride, phosphorus trichloride or boron trifluoride).

According to the method (e), the compound of formula [I] wherein A is a carbonyl group can be obtained.

f. By oxidizing a compound of the formula:

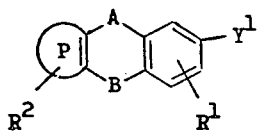   [IX]

wherein A, B, R¹, R² and ring P are as defined above, and Y¹ is a group oxidizable into a carboxyl group such as alkyl (e.g. methyl, ethyl, propyl or butyl), alkanoyl (e.g. acetyl or propionyl), alkenyl (e.g. vinyl or 1-propenyl), formyl, hydroxymethyl or halomethyl (e.g. chloromethyl or bromomethyl).

The oxidation is usually carried out in an inert solvent (e.g. water, pyridine or acetone) in the presence of an appropriate oxidizing agent (e.g. permanganate, chromic acid, dichromate, nitric acid, silver oxide or hypo-hydrohalogenate).

g. By hydrolyzing a compound of the formula:

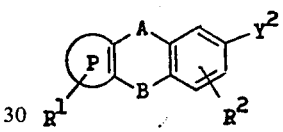   [X]

wherein A, B, R¹, R² and ring P are as defined above, and Y² is a functional group hydrolyzable into a carboxyl group such as alkoxycarbonyl (e.g. methoxycarbonyl, ethoxycarbonyl or isopropoxycarbonyl), carbamoyl or cyano.

The hydrolysis is usually carried out in an inert solvent (e.g. water, aqueous methanol, aqueous dioxane or acetic acid) in the presence of an acid (e.g. hydrochloric acid, sulfuric acid or phosphoric acid) or an alkali (e.g. sodium hydroxide, potassium hydroxide, sodium carbonate or potassium carbonate) at 0°–150°C.

According to the above method (f) or (g), the compound having an OM group wherein M is a hydrogen atom can be obtained.

The compound having an OM group wherein M is a hydrogen atom obtained in accordance with the above method (e), (f) or (g) can be converted in a conventional manner into a corresponding alkyl ester or metal or NH₄ salt.

The above starting compounds can be produced, for example, as follows:

i.

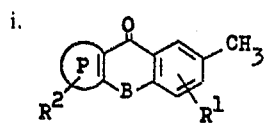 → 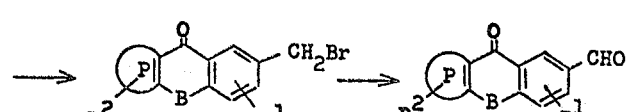

[IXa]   [IXb]   [IXc]

Specific example of the preparation of [IXb] to be used in method (f)

A mixture of 42 g of 7-methyl-5-oxo-5H-[1]benzopyrano[2,3-b]pyridine, 36 g of N-bromosuccinimide, 0.4 g of benzoyl peroxide and 420 ml of carbon tetrachloride is refluxed with stirring under ultraviolet light for 2 hours. The reaction mixture is quickly filtered while it is hot. The crystals are suspended in hot water (about 60°C), and the suspension is thoroughly stirred and filtered again. The crystals are recrystallized from dioxane to give 47.1 g of 7-bromomethyl-5-oxo-5H-[1]benzopyrano[2,3-b]pyridine melting at 211°-212.5°C.

Specific example of the preparation of [IXc] to be used in method (f)

A mixture of 50 g of 7-bromomethyl-5-oxo-5H-[1]benzopyrano[2,3-b]pyridine, 48.4 g of hexamethylenetetramine, 167 ml of water and 167 ml of acetic acid is stirred under reflux for 3 hours. To the reaction mixture is added 100 ml of concentrated hydrochloric acid, and the whole mixture is refluxed for 20 minutes. The reaction mixture is diluted with 200 ml of water, and cooled. The crystalline precipitate is filtered off, washed with water, dried, and then recrystallized from dimethylformamide to give 5-oxo-5H-[1]benzopyrano[2,3-b]pyridine-7-carbaldehyde melting at 233-235°C.

ii.

added to the residue, and the mixture is extracted with chloroform. The chloroform layer is dried, and the chloroform is distilled off. The residue is recrystallized from isopropyl ether or carbon tetrachloride to give 7.5 g of 5H-[1]benzopyrano[2,3-b]pyridine as white crystals melting at 87°-88°C.

Specific example of the preparation of [IIIb] to be used in method (b)

Sodium amide is prepared from 14.5 g of metallic sodium and 0.5 g of ferric nitrate in 1 liter of liquid ammonia, to which is then added 55 g of 5H-[1]benzopyrano[2,3-b]pyridine in small portions. After 20 minutes, 100 mg of methyl iodide is added dropwise to the mixture, and the whole mixture is allowed to stand at room temperature. Water is added to the mixture after the ammonia flies off in vapor, and the mixture is extracted with benzene. The benzene layer is dried, and concentrated, and the residue is recrystallized from a mixture of carbon tetrachloride and isopropyl ether to give 5,5-dimethyl-5H-[1]benzopyrano[2,3-b]pyridine melting at 72°-73°C.

iii.

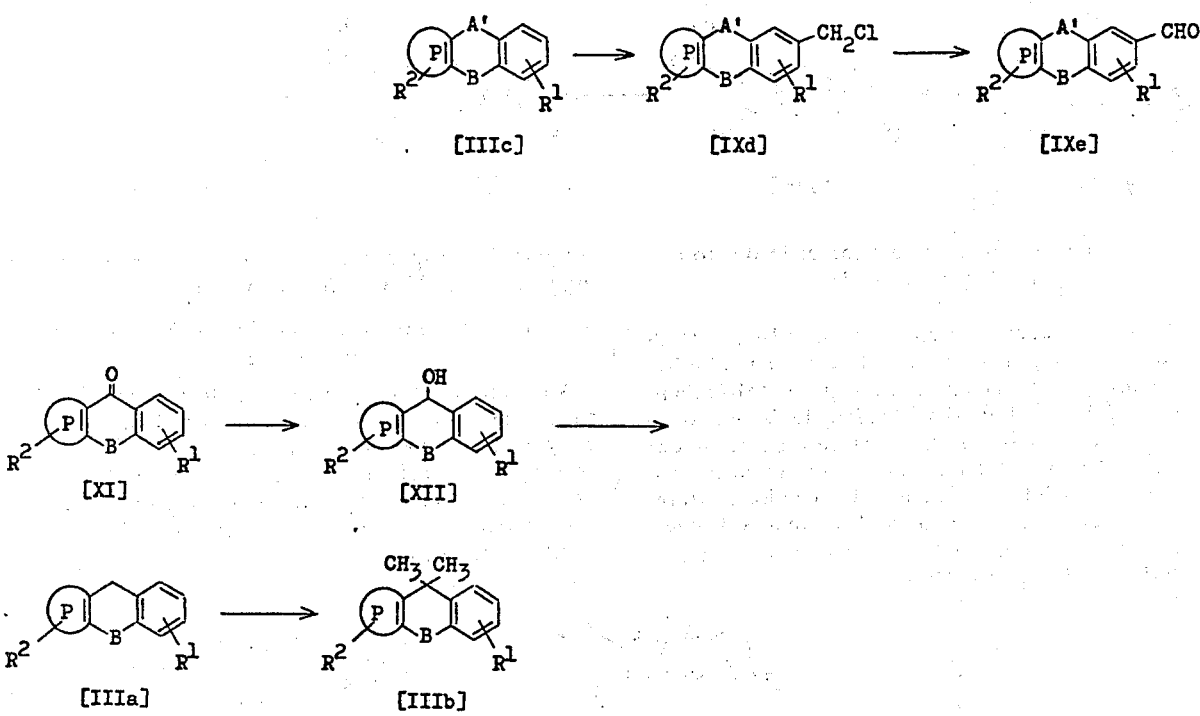

[XI] is reduced to [XII], for example, by the method described in Journal of the Chemical Society, 1952, pages 2057–62.

Specific example of the preparation of [IIIa] to be used in method (b)

A mixture of 10 g of 5-hydroxy-5H-[1]benzopyrano[2,3-b]pyridine, 100 ml of isopropyl alcohol and 10 ml of 20% hydrochloric acid in isopropyl alcohol is refluxed for 3 hours. The reaction mixture is allowed to stand overnight, and then the isopropyl alcohol is removed by distillation under reduced pressure. An aqueous potassium carbonate solution is Specific example of the preparation of [IXd] to be used in method (f)

Hydrogen chloride gas is passed through a mixture of 10 g of 5H-[1]benzopyrano[2,3-b]pyridine, 1.4 g of paraformaldehyde, 110 ml of concentrated sulfuric acid and 22 ml of concentrated hydrochloric acid at 80°C for 12 hours, while 2 g of paraformaldehyde is added in several portions to the reaction mixture. The reaction mixture is poured into water, and the whole mixture is neutralized with sodium carbonate, and extracted with a large amount of chloroform. The chloroform layer is dried, concentrated to 30 ml, and cooled. The crystalline precipitate is filtered off, and recrystallized from chloroform to give 7-chloromethyl-5H-[1]benzopyrano[2,3-b]pyridine melting at 172°–174°C.

Specific example of the preparation of [IXe] to be used in method (f)

A mixture of 52 g of 7-chloromethyl-5H-[1]benzopyrano[2,3-b]pyridine, 63 g of hexamethylenetetramine, 160 ml of water and 160 ml of acetic acid is stirred under reflux for 3 hours. To the reaction mixture is added 80 ml of concentrated hydrochloric acid, and the whole mixture is refluxed for 20 minutes, then diluted with 200 ml of water, and cooled. The crystalline precipitate is filtered off, washed with water, dried, and then recrystallized from dioxane to give 5H-[1]benzopyrano[2,3-b]pyridine-7-carbaldehyde melting at 171°–173°C.

iv.

200 ml of acetone, while the temperature is kept at 10°C. Then the mixture is allowed to stand at 20°C for 1 hour. The reaction mixture is filtered, and the crystalline residue is washed with chloroform. The filtrate and washings are concentrated, and the residue is purified by column chromatography on silica gel with chloroform as eluent, and further by recrystallization from ethanol to give 1-(5-oxo-5H-[1]-benzopyrano[2,3-b]-pyridin-7-yl)-2-methyl-1-propanol melting at 160°C.

v.

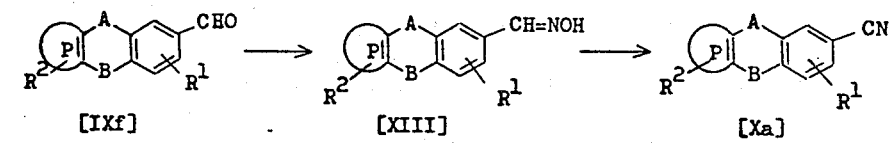

Specific example of the preparation of [XIII]

11 g of hydroxylamine hydrochloride is added to a suspension of 30 g of 5-oxo-5H-[1]benzopyrano[2,3-b]pyridine-7-carbaldehyde in 600 ml of pyridine, and the mixture is vigorously stirred at 80°C for 1 hour. After cooling, the crystals are filtered off, washed with water, and dried to give crude 5-oxo-5H-[1]benzopyrano[2,3-b]pyridine-7-carbaldehyde oxime melting at 254°–256°C with decomposition.

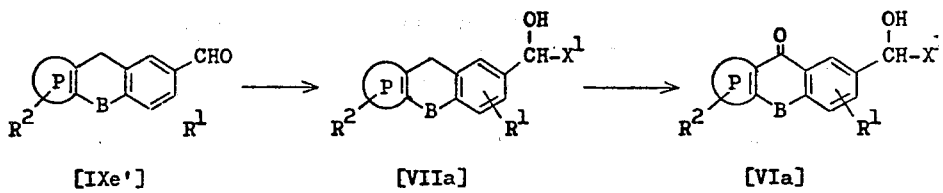

Specific example of the preparation of [VIIa] to be used in method (d)

A Grignard reagent is prepared from 2.14 g of magnesium and 13.1 g of isopropyl iodide in 50 ml of ether in a conventional manner. 12.5 g of 5H-[1]benzopyrano[2,3-b]pyridine-7-carbaldehyde is added to the Grignard reagent, and the mixture is stirred under reflux for 2 hours. After cooling, a saturated ammonium chloride solution is added to the reaction mixture, and the ether layer is separated. The ether is distilled off to give crude 1-(5H-[1]benzopyrano [2,3-b]pyridin-7-yl)-2-methyl-1-propanol.

Specific example of the preparation of [VIa] to be used in method (d)

15 g of potassium permanganate is added in small portions to a solution of 11 g of 1(5H-[1]benzopyrano[2,3-b]pyridin-7-yl)-2-methyl-1-propanol in Specific example of the preparation of [Xa] to be used in method (g)

A mixture of 25 g of 5-oxo-5H-[1]benzopyrano[2,3-b]pyridine-7-carbaldehyde oxime and 150 ml of acetic anhydride is stirred under reflux for 24 hours. After cooling, the crystals are filtered off, washed with water, dried, and recrystallized from dimethylformamide to give 5-oxo-5H-[1]benzopyrano[2,3-b]pyridine-7-carbonitrile melting at 260°C.

vi.

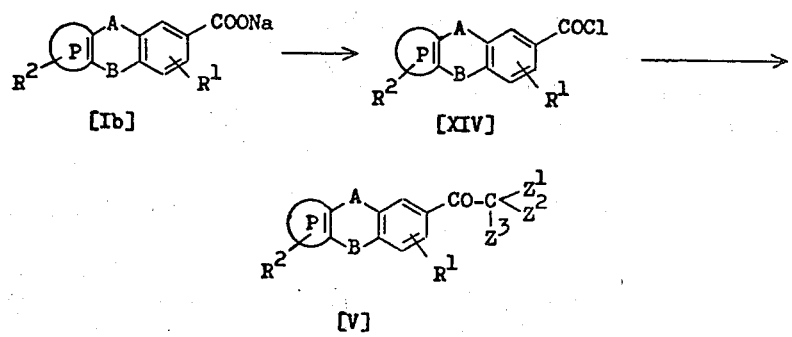

Specific example of the preparation of [XIV]

2.5 g of thionyl chloride is added to a suspension of 4.5 g of sodium 5-oxo-5H-[1]benzopyrano[2,3-b]pyridine-7-carboxylate in 35 ml of carbon tetrachloride with stirring, and the mixture is stirred under reflux for 3 hours. After cooling, the crystals are filtered off, washed with cool water and then with acetone, and dried to give 5-oxo-5H-[1]benzopyrano[2,3-b]pyridine-7-carboxylic acid chloride melting at 234°–235°C.

Specific example of the preparation of [V] to be used in method (c)

0.57 g of magnesium, 0.8 ml of carbon tetrachloride and 3.6 ml of absolute ethanol are placed in a four-necked flask fitted with a dropping funnel, a thermometer, a reflux condenser and a stirrer. 36.5 ml of chlorobenzene is added, and then a mixture of 2.67 g of diethyl malonate, 18 ml of chlorobenzene and 12.6 ml of absolute ethanol is added dropwise, while the temperature is maintained at 65°C. The mixture is allowed to stand at 85°C for 1 hour to complete the reaction. After cooling with water, 4 g of 5-oxo-5H-[1]benzopyrano[2,3-b]pyridine-7-carboxylic acid chloride is added, and the mixture is stirred at 30°–35°C for 1.5 hours. To the reaction mixture is added a mixture of 1 ml of concentrated sulfuric acid and 7 ml of water is added dropwise with stirring under ice cooling, and the precipitate (sodium sulfate) is removed by filtration. The residue is washed with water, dried, and concentrated. The residue is recrystallized from ethanol to give diethyl 2-(5-oxo-5H-[1]benzopyrano[2,3-b]pyridine-7-yl-carbonyl)malonate as white crystals melting at 137°–138.5°C.

vii.

acid dissolves. The solution is evaporated to dryness, and to the residue 14 ml of carbon tetrachloride and 1.43 g of thionyl chloride are added. The mixture is refluxed for 3 hours, and then filtered while it is hot. The filtrated is concentrated, a small amount of carbon tetrachloride is added to the residue to dissolve it, and the solution is allowed to stand at room temperature. Crystals of 2-(p-acetylphenoxy)nicotinoyl chloride precipitate little by little.

The compounds of formula [I] have anti-allergic action as shown, for example, by the following test; in which the alphabetical notations A to D mean the following compounds, respectively:

A: 7-acetyl-5-oxo-5H-[1]benzopyrano[2,3-b]pyridine,

B: 7isobutyryl-5-oxo-5H-[1]benzopyrano[2,3-b]pyridine,

C: 5-oxo-5H-[1]benzopyrano[2,3-b]pyridine-7-carboxylic acid,

D: sodium 2-phenyl-5-oxo-5H-[1]benzopyrano[2,3-b]pyridine-7-carboxylate.

Passive Cutaneous Anaphylaxis Test

The method used was similar to that described by ogilvie (1964). Donryu-strain male rats each weighing 160–200 g were sensitized by the intradermal injection of 0.1 ml of rat serum containing reagin antibody (prepared by the method described by Mota (1964)) diluted 10 times with isotonic sodium chloride solution, 8

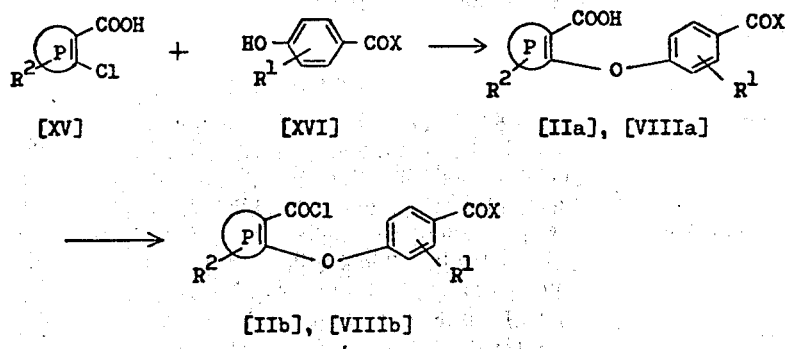

Specific example of the preparation of [IIa] to be used in method (a)

To a solution of 1.03 g of metallic sodium in 27 ml of methanol are added 10 g of p-hydroxyacetophenone and 3.36 g of 2-chloronicotinic acid. The methanol is removed by raising the temperature. The mixture is allowed to stand at 160°–170°C for 2.5 hours. Water is added to the reaction mixture, and the precipitate (excess p-hydroxyacetophenone) is removed by filtration. The filtrate is acidified with hydrochloric acid to yield crystals. The crystals are filtered off, washed with water and chloroform to give 2-(p-acetylphenoxy)nicotinic acid melting at 184°–186°C.

Specific example of the preparation of [IIb] to be used in method (a)

2.56 g of 2-(p-acetylphenoxy)nicotinic acid is suspended in 26 ml of methanol. To the suspension is added a solution of 0.23 g of metallic sodium in 2 ml of methanol. On heating, 2-(p-acetylphenoxy)nicotinic donryu rats being used for each test group. After 48 hours, the animals were challenged, that is a fixed dose of antigen (25 mg egg albumin/kg) and Evans blue dye (12.5 mg/kg) were injected intravenously. A test solution containing a test compound was administered orally 1 hour before, or intraperitoneally 30 minutes before challenge. The animals were killed 30 minutes after challenge, the skin reflected, and the responses measured and scored 0 for diameter of wheal less than 5 mm, 1 for 5–10 mm,* 3 for 15–20 mm and 4 for more than 20 mm. The percentage inhibition was calculated using the formula:

Percent inhibition = $100 - \dfrac{\text{Mean score of treated group}}{\text{Mean score of control group}} \times 100$ The $ED_{50}$, the dose required for 50% inhibition, was calculated from the doseresponse curve.

*: 2 for 10–15 mm.

The results are summarized in the following table:

| Compound | ED₅₀ (mg/kg) | |
|---|---|---|
| | p.o. | i.p. |
| A | 10 | 1.0 |
| B | 25–50 | 1.0 |
| C | 25 | 2.0 |
| D | 40 | 1.0 |

In view of various tests including that mentioned above, the compounds of formula [I] in accordance with the invention can be administered safely as antiallergic agents, either alone or in the form of a pharmaceutical composition consisting essentially of a therapeutically effective amount of the compound in admixture with a suitable and conventional carrier or adjuvant, administratable orally, percutaneously or by way of injection, without harm to the host.

The pharmaceutical composition can take the form of tablets, granules, powder or capsules, for oral administration, of injectable solution for subcutaneous or intramuscular administration, of aerosol inhalant for intranasal administration, or of cream, ointment or jelly for topical administration. The choice of carrier is determined by the prefered form of administration, the solubility of the compounds and standard pharmaceutical practice.

The following is an example of formulations when a compound of the invention is administered for pharmaceutical purposes: 50 mg capsules are prepared from the following composition:

| | |
|---|---|
| Compound [A] | 50 mg |
| Lactose | 45.3 |
| Corn Starch | 40 |
| Talc | 4 |
| Aerosil (SiO₂) | 0.7 |
| | 140.0 mg |

50 ,g tablets are mg from the following composition:

| | |
|---|---|
| Compound [A] | 50 mg |
| Lactose | 32.8 |
| Corn Starch | 36 |
| Microcrystalline Cellulose | 7 |
| Talc | 3 |
| Magnesium Stearate | 0.7 |
| Methyl Cellulose | 0.5 |
| | 130.0 mg |

The tablets may be sugar-coated in a conventional manner. 2% aerosol inhalant are prepared from the following composition:

| | |
|---|---|
| Compound [A] | 2 % |
| Solbitan Trioleate | 0.2 |
| Freon-113 (CCl₂F-CClF₂) | 12.8 |
| Freon-11 (CCl₃F) | 19.5 |
| Freon-12 (CCl₂F₂) | 46 |
| Freon-114 (CClF₂-CClF₂) | 19.5 |
| | 100 % |

2% ointment are prepared from the following composition:

| | |
|---|---|
| Compound [A] | 2 % |
| Purified Water | 34.3 |
| White Petrolatum | 40 |
| Cetanol | 18 |
| Sorbitan Sesquioleate | 5 |
| Lauro Macrogol | 0.5 |
| Ethyl Parahydroxybenzoate | 0.1 |
| Butyl Parahydroxybenzoate | 0.1 |
| | 100 % |

The daily dose of compound [A] lies in the range of 0.5–500 mg per human adult, depending upon the preparation form.

The present invention is further explained by way of the following illustrative examples.

EXAMPLE 1

1.68 g of powdered anhydrous aluminum chloride is added to a solution of 1.15 g of 2-(p-acetylphenoxy)-nicotinoyl chloride in 5 ml of nitrobenzene at 20°–30°C, and the mixture is heated at 80°C for 3.5 hours. After cooling, water is added to the reaction mixture to decompose the aluminum chloride. After removing the nitrobenzene by distillation, the mixture is extracted with chloroform, and the extract is concentrated. The residue is recrystallized from toluene to give 7-acetyl-5-oxo-5H-[1]benzopyrano[2,3-b]pyridine melting at 195-196°C.

EXAMPLE 2

30.5 g of acetyl chloride is placed in a four-necked flask fitted with a stirrer. A mixture of 49 g of crushed aluminum chloride and 20 g of crushed 5H-[1]benzopyrano[2,3-b]pyridine is added in small portions over a period of 30 minutes, keeping the temperature at 10°–20°C by cooling with ice water. After the addition the temperature is raised to 50°–60°C over 1 hour. Violent release of hydrogen chloride takes place. The contents gradually become viscous, and stirring becomes difficult. The contents are allowed to stand at 80°–85°C for 2 hours without stirring. The contents are broken to pieces and thrown into 1 liter of ice water. The crystalline precipitate is filtered off, washed with water, dried, and then recrystallized from ethyl acetate to give 18.5 g of 7-acetyl-5H-[1]benzopyrano[2,3-b]pyridine melting at 142°–144°C.

EXAMPLE 3

9.5 g of powdered aluminum chloride is added in small portions to a mixture of 5 g of 5,5-dimethyl-5H-[1]benzopyrano[2,3-b]pyridine and 5.6 g of acetyl chloride, keeping the temperature at 20°–30°C. The mixture is allowed to stand at 80°C for 1.5 hours, and then poured into ice water. The mixture is extracted with benzene, and the extract is washed with water. The benzene is distilled off, and the crystalline residue is recrystallized from isopropyl ether containing a small amount of carbon tetrachloride to give 4 g of 7-acetyl-5,5-dimethyl-5H-[1]benzopyrano[2,3-b]pyridine melting at 106°–108°C.

EXAMPLE 4

A mixture of 7.5 ml of glacial acetic acid, 0.9 ml of concentrated sulfuric acid, 4.5 ml of water and 4.6 g of diethyl 2-(5-oxo-5H-[1]benzopyrano[2,3-b]pyridin-7-yl-carbonyl)malonate is stirred under reflux for 2 hours. The reaction mixture is poured into 50 ml of cool water. The crystalline precipitate is filtered off, and suspended in water. The suspension is alkalified with 10% sodium hydroxide under ice cooling, and extracted with chloroform. The extract is washed thoroughly with water, dried, and concentrated. The residue is recrystallized from toluene to give 7-acetyl-5-oxo-5H-[1]benzopyrano[2,3-b]pyridine melting at 194°–195°C.

EXAMPLE 5

12.5 g of potassium permanganate is added in small portions to a solution of 9 g of 7-acetyl-5H-[1]benzopyrano[2,3-b]pyridine in 180 ml of acetone at 10°–15°C. The mixture is stirred at room temperature for 1 hour. The reaction mixture is filtered, and the crystalline residue is washed thoroughly with chloroform. The filtrate and washings are concentrated, and the residue is recrystallized from toluene to give 7-acetyl-5-oxo-5H-[1]benzopyrano[2,3-b]pyridine melting at 195°–197°C.

EXAMPLE 6

A mixture of 2.7 g of 2-methyl-1-(5-oxo-5H-[1]benzopyrano[2,3-b]pyridin-7-yl)-1-propanol, 60 ml of acetone and 1.5 g of potassium permanganate is refluxed for 6 hours. The reaction mixture is filtered, and the residue is washed thoroughly was chloroform. The filtrate and washings are concentrated, and the residue is purified by column chromatography on silica gel with chloroform as eluent, and further by recrystallization from ethanol to give 7-isobutyryl-5-oxo-5H-[1]benzopyrano[2,3-b]pyridine melting at 155°–156°C.

EXAMPLE 7

11 g of potassium permanganate is added in small portions to a solution of 6 g of 1-(5H-[1]benzopyrano[2,3-b]pyridin-7-yl)-2-methyl-1-propanol in 160 ml of acetone, and the mixture is stirred at 20°C for 3 hours. The reaction mixture is filtered, and the residue is washed thoroughly with chloroform. The filtrate and washings are concentrated, and the residue is purified by column chromatography on silica gel with chloroform as eluent, and further by recrystallization from acetone to give 7-isobutyryl-5-oxo-5H-[1]benzopyrano[2,3-b]pyridine melting at 155°–156°C.

EXAMPLE 8

A mixture of 2 g of 2-(p-carboxyphenoxy)nicotinic acid and 30 g of concentrated sulfuric acid is stirred at 180°–190°C for 40 minutes on an oil bath. After cooling with water, the reaction mixture is poured into ice water. A jelly-like substance produced crystallizes on heating. The crystals are filtered off, washed thoroughly with water, and recrystallized from aqueous dioxane to give 1.5 g of 5-oxo-5H-[1]benzopyrano[2,3-b]pyridine-7-carboxylic acid melting at 293°–294°C.

EXAMPLE 9

1.7 g of anhydrous aluminum chloride is added in small portions to a solution of 1.2 g of 2-(p-ethoxycarbonylphenoxy)nicotinoyl chloride in 5 ml of nitrobenzene at room temperature with stirring. The mixture is stirred at 80°C for 4 hours, and poured into ice water to decompose aluminum chloride. The nitrobenzene layer is separated, dried over anhydrous magnesium sulfate, and concentrated under reduced pressure. The residue is recrystallized from ethanol to give 0.6 g of ethyl 5-oxo-5H-[1]benzopyrano[2,3-b]pyridine-7-carboxylate melting at 131°–132°C.

EXAMPLE 10

42.4 g of 7-methyl-5-oxo-5H-[1]benzopyrano[2,3-b]pyridine is dissolved in a mixture of 600 ml of pyridine and 600 ml of water with heating. To the solution is added 256 g of potassium permanganate at 90°–95°C with stirring over a period of 2 hours, and the reaction mixture is further stirred at the same temperature for 1 hour. The reaction mixture is filtered while it is hot, and the by-product manganese dioxide is washed thoroughly with hot water. The filtrate and washings are concentrated under reduced pressure, and water is added to dissolve the residue. An insoluble material which is the starting material is removed by filtration, and the filtrate is acidified with hydrochloric acid. The crystalline precipitate is filtered off and recrystallized from a mixture of dioxane and dimethylformamide to give 18 g of 5-oxo-5H-[1]benzopyrano[2,3-b]pyridine-7-carboxylic acid as white needles melting at 293°–294°C.

EXAMPLE 11

A mixture of 0.5 g of 8-methyl-10-oxo-10H-[1]benzopyrano[3,2-c]pyridine and 7 ml of concentrated nitric acid is heated under reflux for 48 hours. The reaction mixture is poured on ice, and adjusted to pH 3 by addition of 10% sodium hydroxide. The crystalline precipitate is filtered off and recrystallized from dimethyl sulfoxide to give 0.25 g of 10-oxo-10H-[1]benzopyrano[3,2-c]pyridine-8-carboxylic acid as white needles melting at above 300°C.

EXAMPLE 12

4.8 g of bromine is added dropwise to a solution of 3.3 g of sodium hydroxide in 28 ml of water at below 0°C, and the mixture is allowed to stand at 0°C for 15 minutes. To the mixture is added dropwise and slowly a solution of 2.4 g of 7-acetyl-5,5-dimethyl-5H-[1]benzopyrano[2,3-b]pyridine in 10 ml of dioxane. The whole mixture is allowed to stand at room temperature for 2 hours, and then the solvent is removed by distillation under reduced pressure. To the residue are added water and benzene, and the mixture is warmed to 30°–40°C. The aqueous layer is neutralized with hydrochloric acid. The crystalline precipitate is recrystallized from aqueous acetic acid to give 1.9 g of 5,5-dimethyl-5H-[1]benzopyrano[2,3-b]pyridine-7-carboxylic acid melting at 241°–242°C.

EXAMPLE 13

A mixture of 3 g of 5-oxo-5H-[1]benzopyrano[2,3-b]pyridine-7-carbonitrile, 30 ml of sulfuric acid, 30 ml of acetic acid and 30 ml of water is heated under reflux for 3 hours. The reaction mixture is poured on ice, and adjusted to pH 3 by addition of 10% sodium hydroxide. The crystalline precipitate is filtered off and recrystallized from a mixture of dioxane and dimethylformamide to give 1.5 g of 5-oxo-5H-[1]benzopyrano[2,3-b]pyridine-7-carboxylic acid melting at 293°–294°C.

EXAMPLE 14

A mixture of 3.4 g of isopropyl 5H-[1]benzopyrano[2,3-b]pyridine-7-carboxylate, 7 ml of concentrated hydrochloric acid and 17 ml of acetic acid is heated under reflux on an oil bath for 3 hours. The reaction mixture is concentrated, and a small amount of water is added to the residue. The mixture is adjusted to pH 2-3 by addition of 10% sodium hydroxide. The crystalline precipitate is filtered off and recrystallized from acetic acid to give 2.5 g of 5H-[1]benzopyrano[2,3-b]pyridine-7-carboxylic acid melting at 285°-286°C.

EXAMPLE 15

A mixture of 10.5 g of 5-oxo-5H-[1]benzopyrano[2,3-b]pyridine-7-carboxylic acid and 150 ml of ethanol is allowed to absorb 10 g of hydrogen chloride gas, and then refluxed for 16 hours. The ethanol is distilled off, and water is added to the crystalline residue. The mixture is extracted with chloroform, and the chloroform layer is washed with aqueous potassium carbonate solution and dried. The chloroform is distilled off, and the residue is recrystallized from ethanol to give ethyl 5-oxo-5H-[1]benzopyrano[2,3-b]pyridine-7-carboxylate melting at 131°-132°C.

EXAMPLE 16

A suspension of 10.8 g of 5-oxo-5H-[1]benzopyrano[2,3-b]pyridine-7-carboxylic acid in 50 ml of water is heated up to 50°-60°C with stirring, and made strongly basic with 10% sodium hydroxide. After cooling to room temperature, the crystalline precipitate is filtered off and recrystallized from a mixture of ethanol and water (1:1) to give 9 g of sodium 5-oxo-5H-[1]benzopyrano 2,3-b]pyridine-7-carboxylate as white crystals melting at above 350°C.

EXAMPLE 17

7.6 ml of nitric acid (specific gravity 1.38) and 7.9 g of potassium permanganate are added to a suspension of 2 g of magnesium oxide in 50 ml of water, and the mixture is heated to 60°C. To the mixture is added 4.5 g of 7-ethyl-5-oxo-5H-[1]benzopyrano[2,3-b]pyridine over a period of 30 minutes with stirring, keeping the temperature at 60°-70°C. After the addition the mixture is stirred at 60°-70°C for 4.5 hours. After cooling, the reaction mixture is filtered under reduced pressure, and the residue containing manganese dioxide is extracted several times with chloroform. The chloroform layer is washed with water, dried, and the chloroform is distilled off. The residue is recrystallized from toluene to give 3.2 g of 7-acetyl-5-oxo-5H-[1]benzopyrano[2,3-b]pyridine melting at 195°-196°C.

Using the procedure set forth in the above examples, but substituting equivalent amounts of the appropriate starting materials, the following compounds are also produced:

1. 7-propionyl-5-oxo-5H-[1]benzopyrano[2,3-b]pyridine, melting at 204°-205°C;
2. 7-isovaleryl-5-oxo-5H-[1]benzopyrano[2,3-b]pyridine, melting at 104°-105°C;
3. 7-cyclopropylcarbonyl-5-oxo-5H-[1]benzopyrano[2,3-b]pyridine, melting at 200°C;
4. 7-cyclohexylcarbonyl-5-oxo-5H-[1]benzopyrano[2,3-b]pyridine, melting at 140°-142°C;
5. 7-acetyl-2-methyl-5-oxo-5-H-[1]benzopyrano[2,3-b]pyridine, melting at 245°-246°C;
6. 7-acetyl-2-methoxy-5-oxo-5H-[1]benzopyrano[2,3-b]pyridine;
7. 7-acetyl-9-chloro-5-oxo-5H-[1]benzopyrano[2,3-b]pyridine, melting at 206°-207°C;
8. 7-acetyl-2-phenyl-5-oxo-5H-[1]benzopyrano[2,3-b]pyridine, melting at 229°-230°C;
9. 7-acetyl-2-(p-methoxyphenyl)-5-oxo-5H-[1]benzopyrano[2,3-b]pyridine;
10. 7-acetyl-2-methyl-5H-[1]benzopyrano[2,3-b]pyridine, melting at 184.5°-185.5°C;
11. 7-acetyl-9-methyl-5H-[1]benzopyrano[2,3-b]pyridine, melting at 135°-137°C;
12. 7-acetyl-9-chloro-5H-[1]benzopyrano[2,3-b]pyridine, melting at 178°-179°C;
13. 7-acetyl-5-oxo-5H-[1]benzothiopyrano[2,3-b]pyridine, melting at 189°-190°C;
14. 7-acetyl-10-methyl-5-oxo-5H,10H-benzo[b][1,8-]naphthyridine, melting at 246°-247°C;
15. 9-methyl-5-oxo-5H-[1]benzopyrano[2,3-b]pyridine-7-carboxylic acid, melting at 304°-306°C;
16. 2-isopropyl-5-oxo-5H-[1]benzopyrano[2,3-b]pyridine-7-carboxylic acid, melting at 250°-253°C;
17. 9-methoxy-5-oxo-5H-[1]benzopyrano[2,3-b]pyridine-7-carboxylic acid;
18. 9-chloro-5-oxo-5H-[1]benzopyrano[2,3-b]pyridine-7-carboxylic acid, melting at 312°-313°C;
19. 2-(p-chlorophenyl)-5-oxo-5H-[1]benzopyrano[2,3-b]pyridine-7-carboxylic acid, melting at above 300°C;
20. 2-(o-tolyl)-5-oxo-5H-1]benzopyrano[2,3-b]pyridine-7-carboxylic acid;
21. sodium 2-phenyl-5-oxo-5H-[1]benzopyrano[2,3-b]pyridine-7-carboxylate, melting at above 250°C;
22. 9-methyl-5-H-[1]benzopyrano[2,3-b]pyridine-7-carboxylic acid, melting at 250°-251°C;
23. 5-oxo-5H-[1]benzothiopyrano[2,3-b]pyridine-7-carboxylic acid, melting at 296°-297°C; and
24. 10-methyl-5-oxo-5H,10H-benzo[b][1,8]naphthyridine-7-carboxylic acid, melting at 308°-309°C with decomposition.

While the invention has been described in detail and with reference to specific embodiments thereof, it will be apparent to one skilled in the art that various changes and modifications can be made therein without departing from the spirit and scope thereof.

What is claimed is:

1. A member selected from the group consisting of chemical compounds of the formula:

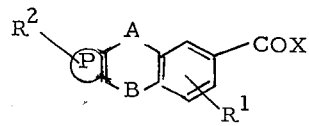

wherein A is a carbonyl group; B is an oxygen atom or a sulfur atom; each of $R^1$ and $R^2$ is a hydrogen atom, a halogen atom, an alkyl group having 1 to 4 carbon atoms, an alkoxy group having 1 to 4 carbon atoms, a phenyl group or a substituted phenyl group, the substituent being selected from the group consisting of a halogen atom, an alkyl group having 1 to 4 carbon atoms and an alkoxy group having 1 to 4 carbon atoms; X is an alkyl group having 1 to 4 carbon atoms, a cycloalkyl group having 3 to 6 carbon atoms or OM (wherein M is a hydrogen atom, an alkyl group having 1 to 4 carbon atoms, a metal atom or $NH_4$); and ring P represents a pyridine ring.
2. A compound of claim 1:
7-acetyl-5-oxo-5H-[1]benzopyrano[2,3-b]pyridine.
3. A compound of claim 1:
7-isobutyryl-5-oxo-5H-[1]benzopyrano[2,3-b]pyridine.
4. A compound of claim 1:
7-acetyl-2-methyl-5-oxo-5H-[1]benzopyrano[2,3-b]pyridine.
5. A compound of claim 1:
7-acetyl-2-phenyl-5-oxo-5H-[1]benzopyrano[2,3-b]pyridine.
6. A compound of claim 1:
5-oxo-5H-[1]benzopyrano[2,3-b]pyridine-7-carboxylic acid.
7. A compound of claim 1:
sodium 5-oxo-5H-[1]benzopyrano[2,3-b]pyridine-7-carboxylate.
8. A compound of claim 1:
9-chloro-5-oxo-5H-[1]benzopyrano[2,3-b]pyridine-7-carboxylic acid.
9. A compound of claim 1:
9-methyl-5-oxo-5H-[1]benzopyrano[2,3-b]pyridine-7-carboxylic acid.
10. A compound of claim 1:
sodium 2-phenyl-5-oxo-5H-[1]benzopyrano[2,3-b]pyridine-7-carboxylate.
11. A compound of claim 1:
5-oxo-5H-[1]benzothiopyrano[2,3-b]pyridine-7-carboxylic acid.

* * * * *